(12) United States Patent
Balboa et al.

(10) Patent No.: US 10,631,851 B2
(45) Date of Patent: Apr. 28, 2020

(54) SUTURE ANCHOR

(71) Applicant: Smith & Nephew, Inc., Memphis, TN (US)

(72) Inventors: Marc Joseph Balboa, Hopkinton, MA (US); Geoffrey Ian Karasic, Milton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 196 days.

(21) Appl. No.: 16/014,647

(22) Filed: Jun. 21, 2018

(65) Prior Publication Data

US 2018/0368827 A1    Dec. 27, 2018

Related U.S. Application Data

(60) Provisional application No. 62/523,291, filed on Jun. 22, 2017.

(51) Int. Cl.
*A61B 17/04* (2006.01)
*A61B 17/00* (2006.01)
*A61B 90/00* (2016.01)

(52) U.S. Cl.
CPC ........... *A61B 17/0401* (2013.01); *A61B 2017/00407* (2013.01); *A61B 2017/042* (2013.01); *A61B 2017/0403* (2013.01); *A61B 2017/044* (2013.01); *A61B 2017/0409* (2013.01); *A61B 2017/0414* (2013.01); *A61B 2017/0445* (2013.01); *A61B 2017/0448* (2013.01);

(Continued)

(58) Field of Classification Search
CPC ........ A61B 17/0401; A61B 2017/0414; A61B 2017/0445; A61B 17/0642; A61B 2017/06019; A61B 2017/0446; A61B 2017/0459; A61B 2017/0462
See application file for complete search history.

(56) References Cited

U.S. PATENT DOCUMENTS

| 5,545,180 A * | 8/1996 | Le | A61B 17/0401 |
| | | | 606/232 |
| 7,713,285 B1 * | 5/2010 | Stone | A61B 17/0401 |
| | | | 606/232 |

(Continued)

*Primary Examiner* — Katrina M Stransky
(74) *Attorney, Agent, or Firm* — Burns & Levinson, LLP; Joseph M. Maraia

(57) ABSTRACT

The present disclosure concerns a suture anchor including a distal body and a proximal body. The distal body defines a bounded transverse eyelet therethrough and the proximal body defines an unbounded transverse eyelet therethrough at a distal end thereof the unbounded transverse eyelet being unbounded distally. The proximal body is cannulated for receiving a proximal portion of the distal body through the cannula, whereby the eyelets are configured for alignment with one another to as to enable receiving a suture therethrough. Once the suture is received, the distal body and proximal body may be rotated relative to one another along a longitudinal axis of the suture anchor such that the eyelets are rotated out of phase with one another causing the suture to wrap around the proximal portion of the distal body and pinching the suture between an outer surface of the distal body and an inner surface of the proximal body. This has the advantage of causing the distal end of the proximal body to expand.

23 Claims, 2 Drawing Sheets

(52) U.S. Cl.
    CPC ............... *A61B 2017/0458* (2013.01); *A61B 2017/0464* (2013.01); *A61B 2090/034* (2016.02)

(56) References Cited

U.S. PATENT DOCUMENTS

| | | | |
|---|---|---|---|
| 2010/0063542 A1* | 3/2010 | van der Burg | A61B 17/0401 606/232 |
| 2010/0331881 A1* | 12/2010 | Hart | A61B 17/0401 606/232 |
| 2014/0277128 A1* | 9/2014 | Moore | A61B 17/0642 606/232 |
| 2017/0112485 A1* | 4/2017 | Housman | A61B 17/0401 |

* cited by examiner

SUTURE ANCHOR

CROSS-REFERENCE TO RELATED APPLICATIONS

This application claims priority to and benefit of U.S. Provisional Application No. 62/523,291, filed Jun. 22, 2017, entitled SUTURE ANCHOR, the contents of which are incorporated herein by reference in their entirety for all purposes.

This application relates to but does not claim priority to U.S. Publication No. 2014-0364905 to Richard M. Lunn, et al., the disclosure of which is incorporated by reference herein in its entirety for all purposes.

BACKGROUND

The present disclosure relates to devices and methods for repairing tissue and in particular, to suture anchors for surgically securing a suture relative to a bone or tissue.

Arthroscopic procedures often require soft tissue to be reattached to bone. To achieve this, anchors are placed in the bone and sutures attached to the anchor are passed through the tissue to securely retain the tissue in place. In conventional implementations the suture is attached to the bone by placing the ends of the suture into a prepared bone hole, and inserting an anchor into the bone hole to provide fixation of the suture. Such suture fixation via interference between the implant and the bone hole is dependent on patient bone quality. Therefore, if the patient bone is of poorer quality, there may be less interference between the anchor and the bone hole and, consequently less fixation of the suture and tissue to bone. Furthermore, poor bone quality can lead to the improper fixation of the anchor itself within the bone hole. Thus, there is a need for improved suture anchors which reduce reliance on patient bone quality and provide for improved fixation of both the suture and the anchor. These and other needs are met by way of the present disclosure.

SUMMARY OF THE DISCLOSURE

In one aspect, the present disclosure relates to a suture anchor. The suture anchor may include a distal body and a proximal body. Advantageously, the distal body may define a bounded transverse eyelet therethrough and the proximal body may define an unbounded transverse eyelet therethrough at a distal end thereof the unbounded transverse eyelet being unbounded distally. The proximal body may be cannulated for receiving a proximal portion of the distal body through the cannula, whereby the eyelets are configured for alignment with one another to as to enable receiving a suture therethrough. Once the suture is received, the distal body and proximal body may be rotatable relative to one another along a longitudinal axis of the suture anchor such that the eyelets are capable of being rotated out of phase with one another causing the suture to wrap around the proximal portion of the distal body and pinching the suture between an outer surface of the distal body and an inner surface of the proximal body. This has the advantage of causing the distal end of the proximal body to expand as discussed herein. In some embodiments, the unbounded transverse eyelet may act as a split point for such expansion of the distal end of the proximal body.

In example embodiments, the eyelets may be elongated and elliptical in shape. In some embodiments, the eyelets are a same configuration, shape or size. In other embodiments, the eyelets may be of different configurations, shapes or sizes. In example embodiments, the aligned eyelets may be configured to allow for translation of the suture received therethrough in only a single direction. Alternatively, the aligned eyelets may be configured to allow for free translation of the suture received therethrough (e.g., in both directions), or to inhibit any such translational motion.

In example embodiments, the distal body may further include a distal portion, wherein the distal portion of the distal body is configured to limit axial advancement of the proximal body over the distal body. Notably, the distal portion may be tapered toward a distal end thereof. In some embodiments, a diameter of a proximal end of the distal portion of the distal body may be greater than a diameter of a distal end of the proximal portion of the distal body (notably, the bounded transverse eyelet may be defined through a junction of the proximal and distal portions of the distal body). In further example embodiments, a proximal end of the distal portion of the distal body may define a proximally facing annular surface which is configured to abut with a distally facing annular surface defined by the distal end of the proximal body thereby limiting axial advancement. In some embodiments, an outer surface of the distal portion of the distal body may be configured to align with an outer surface of the proximal body to form a substantially continuous outer surface of the anchor (for example, the diameter of a proximal end of the distal portion of the distal body may be the same as a diameter of a distal end of the proximal body). In example embodiments, the limiting of axial advancement is configured to align the eyelets with respect to a common position along a longitudinal axis of the anchor.

In further example embodiments, a proximal region of the cannula of the proximal body may be configured to limit axial advancement of the proximal body over the distal body. Thus, in some embodiments, the proximal region of the cannula may have a smaller diameter than a distal region of the cannula. For example, a distal end of the proximal portion of the cannula may define an annular surface inside the cannula which is configured to abut with a distally facing annular surface defined by a proximal end of the proximal portion of the proximal body. Again, in example embodiments, the limiting of axial advancement may be configured to align the eyelets with respect to a common position along a longitudinal axis of the anchor.

In example embodiments, the proximal body and distal body may rotatably coupled relative to one another. In some embodiments, the rotatable coupling may include a clutch or ratchet type mechanism to limit rotational direction. In further embodiments, the rotatable coupling may include a locking mechanism to enable locking rotation once the proximal body is rotated relative to the distal body. In example embodiments, the rotatable coupling may be configured such that rotating the proximal body and distal body relative to one another also result in relative translation along the longitudinal axis. Note that translation beyond an initial axial advancement limitation position may be advantageously enabled by the expansion of the distal end of the proximal body.

BRIEF DESCRIPTION OF THE DRAWINGS

The above and other aspects, features and advantages of the disclosure will be apparent from the following more particular description of examples, as illustrated in the accompanying drawings, in which.

DETAILED DESCRIPTION

Figure 1:
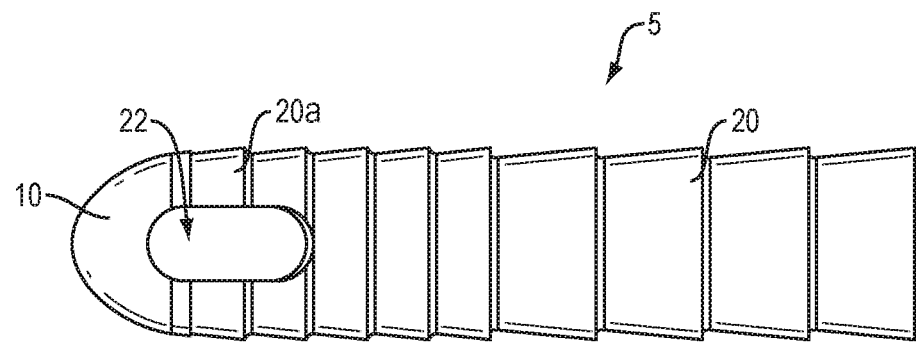
FIG. 1 depicts a side view of an example suture anchor, according to the present disclosure.

In the description that follows, like components have been given the same reference numerals, regardless of whether they are shown in different examples. To illustrate an example(s) of the present invention in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples. The following description of the preferred embodiment(s) is merely exemplary in nature and is in no way intended to limit the disclosure, its application, or uses.

As used in the specification and in the claims, the singular form of "a", "an", and "the" include plural referents unless the context clearly dictates otherwise.

As used in the specification and in the claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue.

Figure 2:
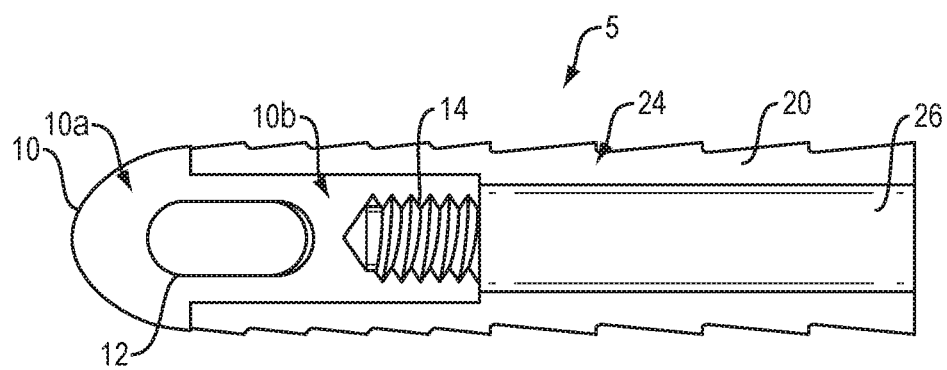
FIG. 2 depicts a cross-sectional view of the example suture anchor of FIG. 1, according to the present disclosure.

Referring to FIGS. 1 and 2, side and side cross-sectional views of an example suture anchor 5 are depicted, respectively. The anchor 5 includes a distal body 10 and a proximal body 20. As can best be seen in the cross-sectional view of FIG. 2, the distal body 10 defines a fully bounded transverse eyelet 12 therethrough. The proximal body 20 is cannulated (cannula 26) and receives a proximal portion 10*b* of the distal body 10 therein so as to enable aligning the bounded transverse eyelet 12 of the distal body 10 with a partially unbounded transverse eyelet 22 defined at a distal end 20*a* of the proximal body 20 (where the unbounded eyelet 22 is unbounded distally). The unbounded eyelet 22 of the proximal body 20 is best seen in FIG. 1. Note that while the eyelets 12 and 22 are depicted as being generally elongated and elliptical they are not limited to such. Indeed any number of geometric configurations may be utilized. Furthermore, respective eyelets 12 and 22 need not have the same configuration, shape or size. Also, while in some embodiments, the suture may be allowed to freely translate when the eyelets are aligned, in other embodiments, translation of the suture may be limited, e.g., to a single direction or prevented.

As shown, the distal body 10 may include both distal portion 10*a* and a proximal portion 10*b*, where the eyelet 12 is defined through a junction of the two. Distal portion 10*a* may be tapered/pointed toward the distal end thereof to facilitate insertion of the anchor 5 into a bone hole. Advantageously, in some embodiments, a diameter of the proximal end of the distal portion 10*a* may be greater than a diameter of a distal end of the proximal portion 10*b*, e.g., such as to allow for only the proximal portion 10*b* of the distal body 10 to enter the lumen of the proximal body 20. For example, in the depicted embodiment, distal portion 10*a* of the distal body 10 defines a proximally facing annular surface which is configured to abut with a distally facing annular surface of the proximal body 20. Note that, in an initial configuration an outer surface of the proximal body 20 and an outer surface of the distal portion 10*a* of the distal body 10 may be aligned to form a substantially continuous outer surface of the anchor 5 (when the proximal portion 10*b* of the distal body 10 is received in the cannula 26 of the proximal body 20). Advantageously, the annular facing surface of the distal portion 10*a* of the distal body 10 may effectively limit axial advancement of the proximal body 20 over the distal body 10 so as to facilitate aligning the eyelets 12 and 22, e.g., with respect to a common position along longitudinal axis of the anchor 5. Furthermore, as best seen in the FIG. 2 the cannula 26 of the proximal body 20 may have a larger diameter toward the distal end (sized and dimensioned to receive the footprint of the proximal portion 10*b* of the distal body 10). A proximal portion of the cannula 26 may have a narrower diameter (e.g., narrower than a diameter of the proximal portion 10*b* of the distal body 10). In this way, the cannula 26, may also serve to limit axial advancement of the proximal body 20 over the distal body 10 so as to facilitate aligning the eyelets 12 and 22, e.g., with respect to a common position along longitudinal axis of the anchor 5. This may be particularly useful to limit axial advancement even where a distal end 20*a* of the proximal body 20 is configured to expand.

It is noted that when the proximal portion 10*b* of the distal body 10 is received in the cannula 26 of the proximal body 20, the distal body 10 and proximal body 20 are configured to be rotatable relative to one another, e.g., along a longitudinal axis of the anchor 5. Thus, in use the eyelets 12 and 22 may be rotated in and out of alignment with one another (e.g., in and out of phase with one another), e.g., using an insertion tool. In example embodiments, the insertion tool may be similar to the insertion tool described with respect to U.S. application Ser. No. 14/006,398. In particular, the inserter may include an outer shaft configured to interface with a proximal portion of the proximal body 20 (e.g., by engaging with an inner geometry of a proximal portion of the cannula 26). The inserter may further include an inner shaft configured to interface with a proximal portion 10*b* of the distal body 10 (e.g., by engaging with an aperture and/or protrusion defined therein, such as engaging threaded aperture 14) simultaneously with the outer shaft interfacing with the proximal body 20. Note that the inner shaft is configured to engage the distal body through the cannula 26 of the proximal body 26. The inserter may be configured so as to allow the inner shaft to be selectively rotated relative to the outer shaft so as to enable rotating of the distal body 10 relative to the proximal body 20. The inserter may further enable rotating the entire anchor 5 or the proximal body 20 relative to a bone hole, e.g., so as to facilitate insertion of the anchor 5 therein. Note that the proximal body 20 may define one or more fixation features 24, such as threads, ridges, wedges, etc. so as to facilitate fixation of the anchor 5 relative to the bone hole.

Figure 3:
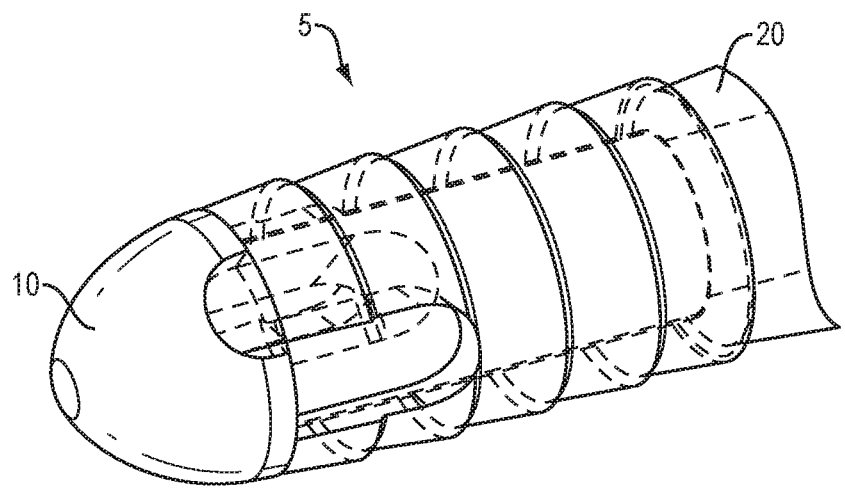
FIG. 3 depicts a rotating proximal and distal bodies of the example suture anchor of FIGS. 1 and 2 relative to one another so as to move eyelets defined on the proximal and distal bodies, respectively, out of phase, according to the present disclosure.
Figure 4:
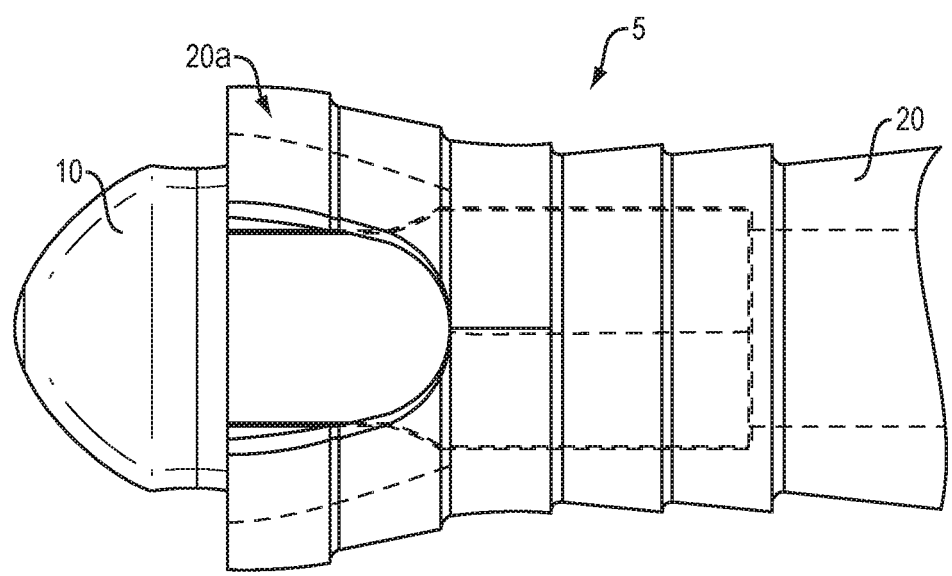
FIG. 4 depicts a distal end of the proximal body of the suture anchor of FIG. 3 expanding as a result of rotating the proximal and distal bodies of the relative to one another, according to the present disclosure.

In order to use the suture anchor 5, the eyelets 12 and 22 may advantageously be aligned for receiving a suture (not depicted). Thus, e.g., the distal body 10 and proximal body 20 may be rotated relative to one another such that the eyelets 12 and 22 are in phase with one another such that a suture can be threaded through both eyelets 12 and 22. As depicted in FIG. 3, once a suture is received through the eyelets 12 and 22, the distal body 10 and proximal body 20 may be rotated relative to one another so that the eyelets 12 and 22 are rotated out of phase one another, thereby pinching the suture between an outer surface of the distal body and an inner surface of the proximal body. As depicted in FIG. 4, in example embodiments, this rotation cases the suture to wrap around the proximal portion of the distal body thereby causing the distal end 20a of the proximal body to expand. Such expansion may advantageously facilitate fixation of the anchor, e.g., relative to a bone hole. Furthermore, such expansion may improve suture fixation. Note that the unbounded nature of the unbounded eyelet 22 advantageously facilitates such expansion without causing excess structural strain. In particular the eyelet acts as a split point for such expansion. The unbounded nature of the unbounded eyelet 22 also allows for such expansion to take place at the distal end 20a with the distal end peeling out as opposed to a bubble region forming at a medial location. The position and configuration of the expansion at the distal end 20a provide for improved fixation relative to medial expansion. Moreover, in some embodiments (not depicted) the expansion may allow for further axial advancement of the proximal body 20 over the distal body 10. Note that in alternative embodiments, the proximal portion 10b of the distal body 10 may be configured to collapse rather than proximal body expand. As an additional advantage, in some embodiments, the wrapping of the suture around the around the proximal portion of the distal body may advantageously shorten a suture length, e.g., between a tissue and the bone so as to improve tension.

In example embodiments, the proximal body 20 and distal body 10 may be rotatably coupled relative to one another. Thus, in some embodiments, a clutch or ratchet type mechanism may be utilized to limit rotational direction. In this way, rotation can be locked once the proximal body 20 is rotated relative to the distal body 10 so as to secure the suture and/or expand the anchor 5 (the suture will not become unwound). This would also allow for rotationally disengaging an insertion tool without accidentally rotating in the reverse direction.

In example embodiments, the proximal body and distal body may be configured such that the bodies are configured to translate relative to one another along the longitudinal axis as well as rotate relative to one another. Thus, in some embodiments, rotating the proximal body and distal body relative to one another may also result in relative translation along the longitudinal axis. A threaded configure, for example, may allow for simultaneous translational and rotational movement. In some embodiment, as noted above, translation may be enabled by the expansion of the anchor.

These and other features and characteristics, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of claims.

What is claimed is:

1. A suture anchor comprising a distal body and a proximal body, the distal body defining a bounded transverse eyelet therethrough and the proximal body defining an unbounded transverse eyelet therethrough at a distal end thereof, wherein the unbounded transverse eyelet being unbounded distally, wherein the proximal body being cannulated and receiving a proximal portion of the distal body through the cannula, whereby the eyelets are configured for alignment with one another to as to enable receiving a suture therethrough, the distal body and proximal body being rotatable relative to one another along a longitudinal axis of the suture anchor such that, once the suture is received through the eyelets, the eyelets are capable of being rotated out of phase with one another causing the suture to wrap around the proximal portion of the distal body and pinching the suture between an outer surface of the distal body and an inner surface of the proximal body thereby causing the distal end of the proximal body to expand.

2. The suture anchor of claim 1, wherein the eyelets are elongated and elliptical in shape.

3. The suture anchor of claim 1, wherein the eyelets are a same configuration, shape or size.

4. The suture anchor of claim 1, wherein the aligned eyelets are configured to allow for translation of the suture received therethrough in only a single direction.

5. The suture anchor of claim 1, wherein the aligned eyelets are configured to allow for free translation of the suture received therethrough.

6. The suture anchor of claim 1, wherein the distal body further includes a distal portion, wherein the distal portion of the distal body is configured to limit axial advancement of the proximal body over the distal body.

7. The suture anchor of claim 6, wherein a diameter of a proximal end of the distal portion of the distal body is greater than a diameter of a distal end of the proximal portion of the distal body.

8. The suture anchor of claim 7, wherein the bounded transverse eyelet is defined through a junction of the proximal and distal portions of the distal body.

9. The suture anchor of claim 6, wherein a proximal end of the distal portion of the distal body defines a proximally facing annular surface which is configured to abut with a distally facing annular surface defined by the distal end of the proximal body thereby limiting axial advancement.

10. The suture anchor of claim 6, wherein an outer surface of the distal portion of the distal body is configured to align with an outer surface of the proximal body to form a substantially continuous outer surface of the anchor.

11. The suture anchor of claim 10, wherein the diameter of a proximal end of the distal portion of the distal body is the same as a diameter of a distal end of the proximal body.

12. The suture anchor of claim 6, wherein the limiting of axial advancement is configured to align the eyelets with respect to a common position along a longitudinal axis of the anchor.

13. The suture anchor of claim 6, wherein the distal portion is tapered toward a distal end thereof.

14. The suture anchor of claim 1, wherein a proximal region of the cannula of the proximal body is configured to limit axial advancement of the proximal body over the distal body.

15. The suture anchor of claim 14, wherein the proximal region of the cannula has a smaller diameter than a distal region of the cannula.

16. The suture anchor of claim 14, wherein a distal end of the proximal portion of the cannula defines an annular surface inside the cannula which is configured to abut with a distally facing annular surface defined by a proximal end of the proximal portion of the proximal body.

17. The suture anchor of claim 14, wherein the limiting of axial advancement is configured to align the eyelets with respect to a common position along a longitudinal axis of the anchor.

18. The suture anchor of claim 1, wherein the unbounded transverse eyelet acts as a split point for such expansion of the distal end of the proximal body.

19. The suture anchor of claim 1, wherein the proximal body and distal body are rotatably coupled relative to one another.

20. The suture anchor of claim 19, wherein the rotatable coupling includes a clutch or ratchet type mechanism to limit rotational direction.

21. The suture anchor of claim 19, wherein the rotatable coupling includes a locking mechanism to enable locking rotation once the proximal body is rotated relative to the distal body.

22. The suture anchor of claim 19, wherein the rotatable coupling is configured such that rotating the proximal body and distal body relative to one another also result in relative translation along the longitudinal axis.

23. The suture anchor of claim 20, wherein translation beyond an initial axial advancement limitation position is enabled by the expansion of the distal end of the proximal body.

* * * * *